(12) United States Patent
Birkner et al.

(10) Patent No.: US 9,371,509 B2
(45) Date of Patent: Jun. 21, 2016

(54) REAGENTS FOR LYSIS OF BACTERIAL CELLS

(75) Inventors: Christian Birkner, Uffing (DE); Herbert von der Eltz, Weilheim (DE); Monika Soukupova, Bernried (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 285 days.

(21) Appl. No.: 12/855,803

(22) Filed: Aug. 13, 2010

(65) Prior Publication Data

US 2011/0053251 A1 Mar. 3, 2011

(30) Foreign Application Priority Data

Sep. 2, 2009 (EP) .................................... 09011264

(51) Int. Cl.
*C12N 1/06* (2006.01)

(52) U.S. Cl.
CPC ........................................ *C12N 1/06* (2013.01)

(58) Field of Classification Search
None
See application file for complete search history.

(56) References Cited

U.S. PATENT DOCUMENTS

| 5,185,153 A * | 2/1993 | Pollock .......................... 424/440 |
| 7,951,598 B2 * | 5/2011 | Kobold et al. .................. 436/63 |
| 8,101,744 B2 * | 1/2012 | Birkner et al. ............... 536/25.4 |

FOREIGN PATENT DOCUMENTS

EP    1983051 A3    10/2008

OTHER PUBLICATIONS

Pitcher et al. "Rapid extraction of bacterial genomic DNA with guanidium thiocyanate". Letters in Applied Microbiology.1989. 8: 151-156.*
Martin et al. Luminescnece. 2001 (16): pp. 29-32.*
Docherty, Katheryn M. and Kulpa, Charles F. Jr., Toxicity and antimicrobial activity of imidazolium and pyridinium ionic liquids, Green Chemistry, 2005, pp. 185-189, vol. 7.
Ranke, J. et al., Biological effects of imidazolium ionic liquids with varying chain lengths in acute Vibrio fischeri and WST-1 cell viability assays, Ecotoxicology and Environmental Safety, 2004, pp. 396-404, vol. 58.
Stepnowski, P. et al., Evaluating the cytotoxicity of ionic liquids using human cell line HeLa, Human & Experimental Toxicology, 2004, pp. 513-517, vol. 23.

* cited by examiner

*Primary Examiner* — Vera Afremova
(74) *Attorney, Agent, or Firm* — Dinsmore & Shohl LLP (57) ABSTRACT

The invention provides a composition containing an aqueous liquid phase, bacterial cells, and an ionic compound dissolved in the liquid phase. The ionic compound is selected from the group consisting of 1-butyl-3-methyl-imidazolium-thiocyanate, 1-butyl-3-methyl-imidazolium-2(2-methoxy-ethoxy)ethylsulfate, 1-methyl-1-[4-(3-methyl-3H-imidazol-1-ium)-but-1-yl]-3H-imidazolium-di(toluylsulfate), and 1-butyl-3-methyl-imidazolium-octylsulfate. The compositions of the invention are advantageously used for preparing lysates of biological cells, particularly bacterial cells.

10 Claims, 4 Drawing Sheets

REAGENTS FOR LYSIS OF BACTERIAL CELLS

RELATED APPLICATIONS

This application claims priority to European application EP 09011264.0 filed Sep. 2, 2009.

FIELD OF THE INVENTION

The present invention relates to reagents and compositions effective in lysing biological cells. A particular objective underlying the present invention is the provision of lysis reagents capable of lysing bacterial cells in the absence of lytic enzymes such as (but not limited to) a peptidoglycan degrading enzyme.

BACKGROUND OF THE INVENTION

The invention provides a composition comprising an aqueous liquid phase, bacterial cells, and an ionic compound dissolved in the liquid phase, characterized in that the ionic compound is selected from the group consisting of 1-butyl-3-methyl-imidazolium-thiocyanate, 1-butyl-3-methyl-imidazolium-2(2-methoxy-ethoxy)ethylsulfate, 1-methyl-1-[4-(3-methyl-3H-imidazol-1-ium)-but-1-yl]-3H-imidazolium-di(toluylsulfate), and 1-butyl-3-methyl-imidazolium-octylsulfate. The compositions of the invention are advantageously used for preparing lysates of biological cells, particularly bacterial cells.

In the biochemical process of purifying an analyte from an intracellular compartment cell lysis is one of the first steps to be performed and of major importance. Concerning the purity and yield of the finally obtained analyte, the way of performing lysis has a significant impact on these parameters. The methods of the state of the art to effect cell lysis are largely based on mechanical and/or enzymatic treatment of the sample material. In addition, various chemical substances are known to the state of the art for the disintegration of cellular structure and the liberation of analytes. Examples therefore are chaotropic agents and detergents. In the case one or more analytes are to be purified from bacterial cells, the skilled person it is faced with a number of problems which are generated by the specific features of these cells.

Bacteria are a large group of unicellular microorganisms. Typically a few micrometers in length, bacteria have a wide range of shapes, ranging from spheres to rods and spirals. The bacterial cell is surrounded by a lipid membrane, or cell membrane (also referred to as the cytoplasmic membrane), which encloses the contents of the cell and acts as a barrier to hold nutrients, proteins, nucleic acids and other essential components of the cytoplasm within the cell. As they are prokaryotes, bacteria do not tend to have membrane-bound organelles in their cytoplasm and thus contain few large intracellular structures.

In most but not all bacteria a bacterial cell wall covers the outside of the cell membrane. The cell wall is a tough, flexible or rigid layer that surrounds the cell membrane. Thus, it is located outside the cell membrane and provides the cell with structural support and protection, and also acts as a filtering mechanism. The cell wall is essential to the survival of many bacteria. A major function of the cell wall is to act as a pressure vessel, preventing over-expansion when water enters the cell. Bacterial cell walls are made of peptidoglycan (also known as murein) as the major component. The peptidoglycan is synthesized from polysaccharide chains cross-linked by certain peptides containing D-amino acids. Bacterial cell walls are different from the cell walls of plants and fungi, which are made of cellulose and chitin, respectively. The bacterial cell wall is also distinct from that of Archaea, which do not contain peptidoglycan.

Gram staining is an empirical method of differentiating bacterial species into Gram-positive and Gram-negative, based on the chemical and physical properties of their cell walls. While Gram staining is a valuable diagnostic tool in both clinical and research settings, not all bacteria can be definitively classified by this technique, thus forming Gram variable and Gram indeterminant groups as well.

Gram-positive bacteria possess thick mesh-like cell walls containing many layers of peptidoglycan and teichoic acids. The cell walls of Gram-positive bacteria appear purple upon Gram staining. In contrast, Gram-negative have a thin cell wall consisting of only a few layers of peptidoglycan surrounded by a second lipid membrane containing lipopolysaccharides and lipoproteins. The cell walls of Gram-negative bacteria stain pink.

In order to purify an analyte from an intracellular compartment of bacterial cells, several methods are known to break up the cells and to release their cytoplasmic components.

Mechanical methods frequently rely on the use of a bead mill break up the material by grinding. At the same time, significant shearing forces are generated. Depending on the analyte to be isolated, shearing is a disadvantage, e.g., when nucleic acids are to be purified.

Liquid-based homogenization is the most widely used cell disruption technique for small volumes. Cells are lysed by forcing the cell or tissue suspension through a narrow space, thereby shearing the cell walls and membranes. Three different types of homogenizers are known in the state of the art. A Dounce homogenizer consists of a round glass pestle that is manually driven into a glass tube. A Potter-Elvehjem homogenizer consists of a manually or mechanically driven pestle shaped to fit a rounded or conical vessel. The number of strokes and the speed at which the strokes are administered influences the effectiveness of Dounce and Potter-Elvehjem homogenization methods. However, owing to largely manual operation, these homogenizers are not suited for high throughput of samples. Also, processing of very small sample volumes is difficult.

A French press consists of a piston that is used to apply high pressure to a sample volume, forcing it through a tiny hole in the press. The French press is often the method of choice for breaking bacterial cells mechanically. However, the device is expensive and also not suited for sample preparation with high throughput.

Sonication is another method of physical disruption commonly used to break open cells. The method uses pulsed, high frequency sound waves to agitate and lyse the bacteria and sometimes even spores. The sound waves are delivered using an apparatus with a vibrating probe that is immersed in the liquid cell suspension. Mechanical energy from the probe initiates the formation of microscopic vapor bubbles that form momentarily and implode, causing shock waves to radiate through a sample. To prevent excessive heating, ultrasonic treatment is applied in multiple short bursts to a sample immersed in an ice bath.

Alternatively, the freeze/thaw method can be used to lyse bacterial cells. The technique involves freezing a cell suspension in a dry ice/ethanol bath or freezer and then thawing the material at room temperature or 37° C. This method of lysis causes cells to swell and ultimately break as ice crystals form during the freezing process and then contract during thawing. Multiple cycles are necessary for efficient lysis, and the process can be quite lengthy.

In order to make the lysis process more efficient, cells can additionally be incubated with lysozyme (N-acetylmuramide glycanhydrolase), whereby the cell walls are degraded. The enzyme functions by attacking peptidoglycans (found in the cells walls of bacteria, especially Gram-positive bacteria) and hydrolyzing the glycosidic bond that connects N-acetylmuramic acid with the fourth carbon atom of N-acetylglucosamine.

Detergents are other additives used in the processes of lysing a sample containing bacterial cells. However, a detergent frequently produces foam which is not desired in such processes. Also, certain detergents denature proteins. This is a disadvantage in case a protein analyte is purified. The same applies to the use of chaotropic agents as additives.

The methods of the state of the art for lysing bacterial cells have certain disadvantages. It was therefore an object of the invention to provide alternative methods which at least in part overcome these disadvantages. Particularly, it was an object of the invention to provide a method for lysing Gram-positive and/or Gram-negative bacterial cells. It was a further object of the invention to provide a method for lysing bacterial cells in a small volume.

In case the sample material not only comprises bacterial cells but also other cell types, e.g., yeast cells, it is often desired to use the methods for lysing cells which is selective for the target cells. Thereby, the amount of undesired byproducts released from other cells but the target cells can favorably be reduced. A further object of the invention therefore was to provide a method for cell lysis which is specific for bacterial cells but not for other microbial cells such as fungal or yeast cells.

SUMMARY OF THE INVENTION

According to the invention, one or more of the above-mentioned objectives were met by the embodiments of the present invention.

A first aspect of the invention is a composition comprising an aqueous liquid phase, bacterial cells, and an ionic compound dissolved in the liquid phase at a concentration of about 560 mM or higher, characterized in that the ionic compound is selected from the group consisting of 1-butyl-3-methyl-imidazolium-thiocyanate, 1-butyl-3-methyl-imidazolium-2(2-methoxyethoxy)ethylsulfate, 1-methyl-1-[4-(3-methyl-3H-imidazol-1-ium)-but-1-yl]-3H-imidazolium-di(toluylsulfate), and 1-butyl-3-methyl-imidazolium-octylsulfate.

A second aspect of the invention is the use of a composition comprising an aqueous liquid phase and an ionic compound dissolved in the liquid phase at a concentration of about 560 mM or higher, for destroying the cell wall of a bacterial cell, whereby the ionic compound is selected from the group consisting of 1-butyl-3-methyl-imidazolium-thiocyanate, 1-butyl-3-methyl-imidazolium-2(2-methoxy-ethoxy)ethylsulfate, 1-methyl-1-[4-(3-methyl-3H-imidazol-1-ium)-but-1-yl]-3H-imidazolium-di(toluylsulfate), and 1-butyl-3-methyl-imidazolium-octylsulfate.

A third aspect of the invention is a method of producing a lysate of a bacterial cell, the method comprising (a) contacting the bacterial cell with, a composition comprising an aqueous liquid phase and an ionic compound dissolved in the liquid phase at a concentration of about 560 mM or higher, whereby the ionic compound is selected from the group consisting of 1-butyl-3-methyl-imidazolium-thiocyanate, 1-butyl-3-methyl-imidazolium-2(2-methoxyethoxy)ethylsulfate, 1-methyl-1-[4-(3-methyl-3H-imidazol-1-ium)-but-1-yl]-3H-imidazolium-di(toluylsulfate), and 1-butyl-3-methyl-imidazolium-octylsulfate, and (b) incubating the bacterial cell with the liquid phase, thereby producing a lysate of the bacterial cell.

A fourth aspect of the invention is a composition comprising an aqueous liquid phase, Gram-negative bacterial cells, and an ionic compound dissolved in the liquid phase at a concentration of about 370 mM or higher, characterized in that the ionic compound is 1-butyl-3-methyl-imidazolium-octylsulfate.

A fifth aspect of the invention is the use of a composition according to the invention for destroying the cell wall of a Gram-negative bacterial cell.

A sixth aspect of the invention is a method of producing a lysate of a Gram-negative bacterial cell, the method comprising (a) contacting the bacterial cell with a composition comprising an aqueous liquid phase and an ionic compound dissolved in the liquid phase at a concentration of about 370 mM or higher, whereby the ionic compound is 1-butyl-3-methyl-imidazolium-octylsulfate, and (b) incubating the bacterial cell with the liquid phase, thereby producing a lysate of the Gram-negative bacterial cell.

A seventh aspect of the invention is a method method of purifying a nucleic acid from a cell, comprising the steps of (a) destroying the cell wall of the cell if a cell wall is present; (b) contacting and incubating the cell with an acidic aqueous solution comprising 1-butyl-3-methyl-imidazolium-thiocyanate at a concentration of 1.5 M or higher, thereby forming a lysate; (c) contacting the lysate with a solid phase comprising a silica surface, whereby the nucleic acid is adsorbed to the surface; (d) separating the solid phase from the liquid phase and optionally washing the solid phase, whereby the nucleic acid remains adsorbed thereto; and (e) eluting the nucleic acid from the solid phase, thereby purifying the nucleic acid.

DETAILED DESCRIPTION OF THE INVENTION

Certain terms are used with particular meaning, or are defined for the first time, in this description of the present invention. For the purposes of the present invention, the terms used are defined by their art-accepted definitions, when such exist, except that when those definitions conflict or partially conflict with the definitions set forth below. In the event of a conflict in definition, the meaning of a terms is first defined by any of the definitions set forth below.

The term "comprising" is used in the description of the invention and in the claims to mean "including, but not necessarily limited to".

The articles "a" and "an" are used herein to refer to one or to more than one (i.e., to at least one) of the grammatical object of the article. By way of example, "a cation" means one cation or more than one cation.

When designating a range of numerical values such as a concentration range, the range can be indicated by the word "between", followed by a first value $n_1$, the word "and", and a second value $n_2$. In addition, the designated range can be indicated by the expression "in the range of $n_1$ to $n_2$". If not stated otherwise, when a designated range is indicated, the lower boundary of the designated range is understood as being the value either equal to, or higher than the first value. The higher boundary of the designated range is understood as being either the value equal to, or lower than the second value". Thus, a value x in the designated range is given by $n_1 \leq x \leq n_2$.

Further, it is understood that the term "about" in combination with a numerical value n indicates a value x in the interval given by the numerical value ±5% of the value, i.e., $n-0.05*n \leq x \leq n+0.05*n$. In case the term "about" in combination with a numerical value n describes a preferred embodiment of the invention, the value of n is most preferred, if not indicated otherwise.

The invention encompasses processes for lysing cells, i.e., formation of a lysate therefrom. A "lysate" or a "lysed sample" can be obtained from a complex sample and/or biological sample material comprising cells, preferably microbial cells, and very much preferred bacterial cells, whereby the structural integrity of a substantial portion of the cells present is disrupted. To this end, the cell wall, if present, has to be destroyed. To release the contents of disrupted bacterial cells the material is treated with certain chemicals to disintegrate, make porous, dissolve, degrade or denature the cell walls of the microbial cells. In addition, the cellular membranes have to be destroyed. However, after removal of the cell wall bacterial cells are very unstable, typically owing to the lack of the pressure vessel function and water influx from the outside through the cell membrane. Cells having their cell walls removed therefore quickly burst, whereby cytoplasmic components are released. These processes are encompassed by the term "lysis".

In case there remains particulate, i.e., undissolved matter of the sample material following the lysis process, the particulate matter is usually separated from the lysate to result in a cleared lysate. This can be done, e.g, by way of filtering or centrifugation. In such a case the cleared lysate is processed further, e.g., by purifying a bacterial analyte (e.g., a nucleic acid) from the lysate. In the context of the present invention, the term "lysate" encompasses a cleared lysate.

A preferred analyte to be purified from the lysates according to the invention is a nucleic acid. The term "nucleic acid" as used within this application denotes DNA and RNA, and mixtures thereof.

In order to purify nucleic acids from a lysate the state of the art provides methods making use of a chaotropic agent such as a guanidine salt and/or anionic, cationic, zwitterionic or non-ionic detergent when nucleic acids are set free in the lysis process. In some instances it is considered an advantage to additionally use a protease which rapidly degrades enzymes with nucleolytic activity and other unwanted proteins.

Another preferred analyte to be purified from the lysates according to the invention is selected from the group consisting of a bacterial protein, a recombinantly expressed protein, a lipid, an organic compound with a low-molecular-weight of between about 50 Da (Daltons) and about 20,000 Da, said organic compound being of bacterial origin, and an anorganic cytoplasmic compound.

The term "adsorption"/"adsorbing" generally means adhere or attach molecules or ions, the "solute" dissolved in a liquid phase, to a surfaces or an interface of a solid phase. It is a surface process such that the accumulating molecules do not actually penetrate the substance to which they are adsorbed. The term "adsorption" is therefore not to be confused with absorption which means the filling of pores in a solid phase. Adsorption increases the concentration of the solute in the vicinity of the surface of the solid phase over the concentration in the bulk of the liquid phase, due to the attractive interaction between the solid phase immersed into the liquid phase with the solute. The binding to the surface is usually weak and reversible. Matter adsorbed on the surface of the solid phase can be "eluted" therefrom by altering or exchanging the liquid phase the solid phase is immersed in. Conditions can be changed as to desorb the molecules from the solid phase. This process is also referred to as "elution" of the molecules from the solid phase.

The term "solid phase" to which a nucleic acid is adsorbed is understood as being a substrate which is insoluble in the liquid compositions according to the invention. A preferred solid phase is a substrate with a surface capable of interacting with the phosphate groups of the backbone of nucleic acids. The solid phase may be in the form of porous or non-porous particles, powdered particles, or fibers. A solid phase consisting of fleece material which comprises a plurality of non-woven fibers is also encompassed. Preferred solid phases are porous and/or non-porous mineral substrates such as silica, or other materials with oxidic surfaces (including, but not limited to, zirconium oxide, aluminum oxide, and other metal oxides), or mixtures thereof. Preferred solid phases consist of glass. The term "solid phase" further encompasses magnetically attractable particles coated with an oxidic surface material, such as, but not limited to, silica. The term "magnetically attractable particle" denotes a particle with magnetic, paramagnetic or superparamagnetic properties. In a preferred embodiment, the particle is magnetically displaceable but does not retain any magnetization in the absence of an externally applied magnetic field. Further, it is understood that a substrate in the form of "powder" or "powdered" material refers to finely divided material which, when dispersed in a liquid composition, produces a suspension. The term "powder" or "powdered" material is intended to include tablets, in which the powdered material has been aggregated, but still yields a suspension when combined with a liquid composition. The term "silica" as used within this application denotes materials which are mainly build up of silicon and oxygen. These materials comprise silica, silicon dioxide, silica gel, fumed silica gel, diatomaceous earth, celite, talc, quartz, glass, and glass particles, including all different compositions, forms and shapes of these materials. Glass particles, for example, may comprise particles of crystalline silica, soda-lime glasses, borosilicate glasses, and fibrous, non-woven glass.

The terms "aqueous", "aqueous" phase and "aqueous" solution describe a liquid phase of which the solvent portion comprises water. However, other solvents such as a water-miscible organic solvent or an ionic liquid can be present in the solvent portion, too. In a preferred embodiment and in view of the presence of other solvents or ionic liquids in a solution, it is considered "aqueous" if between 20% and 100% of the solvent portion, measured as volume by volume [v/v], is water. That is to say, according to the invention an aqueous liquid phase preferably contains water in a relative amount of at least 20% [v/v], also preferred at least 30% [v/v], also preferred at least 50% [v/v], also preferred at least 75% [v/v], also preferred at least 90% [v/v].

An "ionic liquid" is a liquid that contains only ions. In the broad sense, this term includes all the molten salts, for instance, sodium chloride at temperatures higher than 800° C. However, in the context of the present invention the term "ionic liquid" is understood as denoting a salt whose melting point is lower such that at room temperature the salt is in a liquid state of aggregation. In addition, the ionic liquid in the context of the invention is a water-soluble ionic liquid. The term "ionic liquid" at the same time denotes a salt composed of a cation and an anion. The anion can be an anorganic or organic anion, the cation is mostly an organic cation, but in any case one ion (anion or cation) is an organic ion. The cation may comprise imidazolium cations, pyridinium cations, ammonium cations, phosphonium cations and substituted guanidinium cations. At least one ion of the ion pair has a delocalized charge. Due to the weak interactions between both ions, ionic liquids display a low melting point.

Owing to their chemical structure, ionic liquids can act as solvents for hydrophilic and for hydrophobic compounds. Ionic liquids, particularly those with an organic ionic portion can be used as detergent-like compounds. Interestingly, such compounds can often be dissolved in solutions at much higher concentrations as conventional detergents in known lysis reagents.

The present invention provides novel aqueous compositions comprising certain ionic liquids as lysis reagents. That is to say, the bacterial peptidoglycan-containing cell walls are destroyed when contacted with an aqueous solution containing a ionic compound selected from the group consisting of 1-butyl-3-methyl-imidazolium-thiocyanate (Formula 1), 1-butyl-3-methyl-imidazolium-2(2-methoxyethoxy)ethylsulfate (Formula 2), 1-methyl-1-[4-(3-methyl-3H-imidazol-1-ium)-but-1-yl]-3H-imidazolium-di(toluylsulfate) (Formula 3), and 1-butyl-3-methyl-imidazolium-octylsulfate (Formula 4). In this context, the verb "destroy" is understood as encompassing the meanings of disintegrate, make porous, dissolve, degrade, and denature.

Bacterial cell walls of both Gram-positive and gram-negative cells are destroyed when incubated with Guanidine thiocyanate (GuaSCN) present in a concentration of about 2.25 M. At a concentration of 375 mM, GuaSCN is ineffective to this end.

Figure 1:
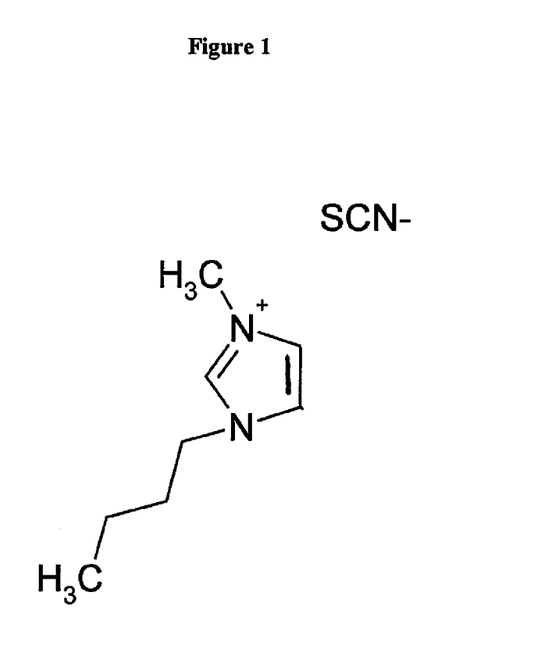
FIG. 1: 1-butyl-3-methyl-imidazolium-thiocyanate (Formula 1)
Figure 2:
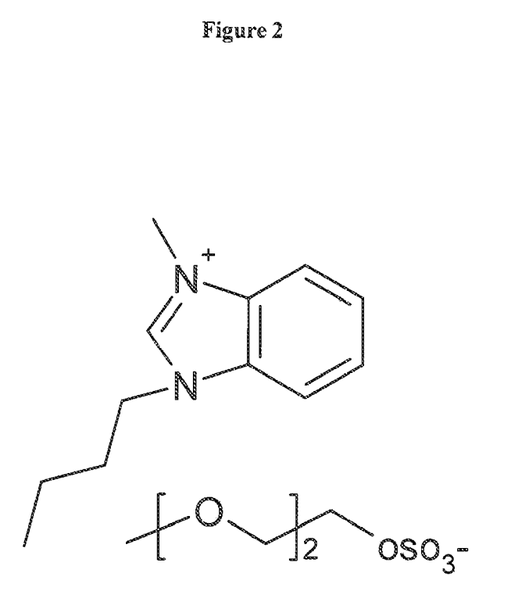
FIG. 2: 1-butyl-3-methyl-imidazolium-2(2-methoxyethoxy)ethylsulfate (Formula 2)

The inventors have found that interestingly not any ionic liquid with an organic ionic component is capable of destroying a bacterial cell wall in the same way. As can be seen in Table 2 (Example 4), among the tested compounds there are two, namely 1-butyl-3-methyl-imidazolium-thiocyanate (BMIM-SCN) (Formula 1) and 1-butyl-3-methyl-imidazolium-2(2-methoxyethoxy)-ethylsulfate (Formula 2), which destroy the cell walls of both Gram-positive and Gram-negative cells.

However, in the case of BMIM-SCN (Formula 1) (L1.1-3, see Examples 3 and 4) both types of cell walls are destroyed only when this compound is present in the lysis reagent at a concentration of 3 M, corresponding to about 2.25 M in the mixture with the bacterial suspension. To achieve the same result, surprisingly only a quarter of this concentration is required when ECOENG™41M (Formula 2) (present in the lysis reagent L2.1) is used as the active ingredient. The reasons for this remarkable effect are not clear at the moment.

The effectiveness of BMIM-SCN (Formula 1) in destroying bacterial cell walls is comparable with that of GuaSCN, in that a concentration in the mixture of 375 mM also falls short of destroying bacterial cell walls. However, surprisingly, when the concentration of BMIM-SCN (Formula 1) is increased by about 50% an interesting effect is observed. At a concentration of about 562.5 mM in the mixture, Gram-negative cells are lysed, their cell walls are destroyed. Thus, the present invention provides a lysis solution for Gram-negative bacteria comprising a measured amount of BMIM-SCN (Formula 1) in the presence of the bacteria, the concentration of BMIM-SCN (Formula 1) being higher than 375 mM and equal to or smaller than about 562.5 mM. In addition, the present invention provides a lysis solution for Gram-negative bacteria comprising a measured amount of BMIM-SCN (Formula 1) in the presence of the bacteria, the concentration of BMIM-SCN (Formula 1) being higher than 562.5 mM and equal to or smaller than about 2.25 M. Notwithstanding, higher concentrations of BMIM-SCN (Formula 1) are also possible, in order to achieve the desired result, and are therefore encompassed by the present invention.

Figure 4:
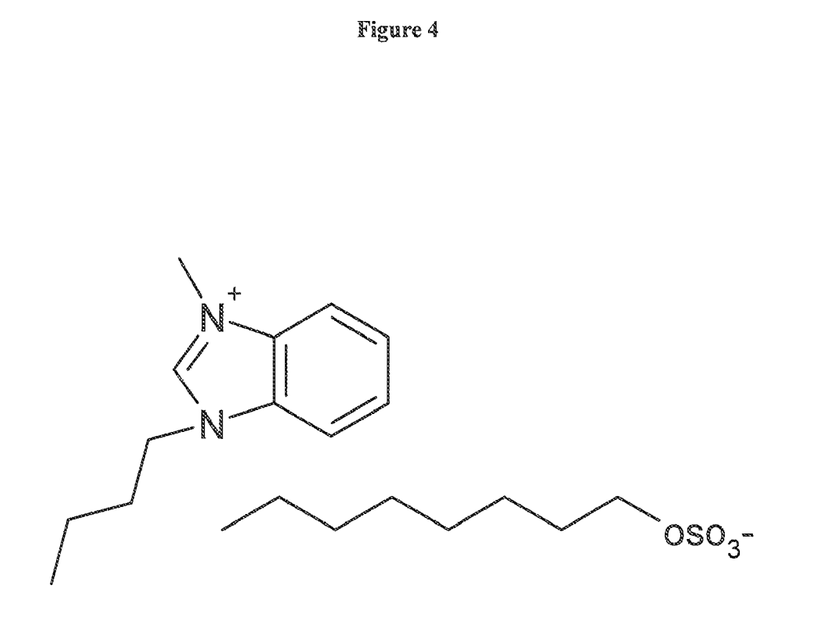
FIG. 4: 1-butyl-3-methyl-imidazolium-octylsulfate (Formula 4)

Another concentration-dependent effect can be seen with 1-butyl-3-methyl-imidazolium-octylsulfate (Formula 4) (present in the lysis reagents L4.1 and L4.2). At a concentration of 247.5 mM or lower the compound falls short of destroying bacterial cell walls. However, at a concentration higher than 247.5 mM and up to 375 mM the compound becomes capable of destroying the cell walls of Gram-negative bacteria. Once the critical concentration is reached, the lysis result is achieved. However, contrary to BMIM-SCN (Formula 1), no concentration was found where additionally the cell walls of Gram-positive bacteria were destroyed. The invention therefore provides a lysis solution for Gram-negative bacteria comprising a measured amount of 1-butyl-3-methyl-imidazolium-octylsulfate (Formula 4) in the presence of the bacteria, the concentration of 1-butyl-3-methyl-imidazolium-octylsulfate (Formula 4) being higher than 247.5 mM and equal to or smaller than about 375 mM. In addition, the present invention provides a lysis solution for Gram-negative bacteria comprising a measured amount of 1-butyl-3-methyl-imidazolium-octylsulfate (Formula 4) in the presence of the bacteria, the concentration of 1-butyl-3-methyl-imidazolium-octylsulfate being higher than 375 mM and equal to or smaller than about 1.7 M.

Figure 3:
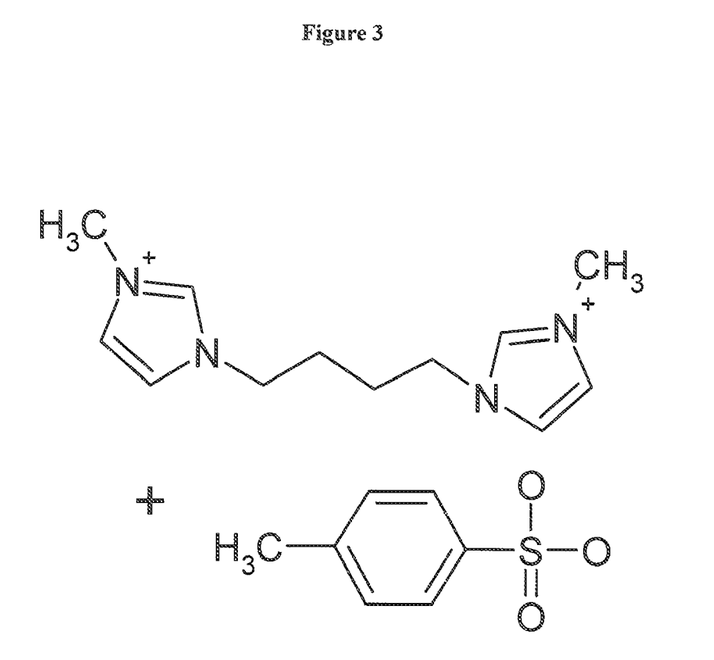
FIG. 3: 1-methyl-1-[4-(3-methyl-3H-imidazol-1-ium)-but-1-yl]-3H-imidazolium-di(toluylsulfate) (Formula 3)

Completely unexpected and very surprisingly, 1-methyl-1-[4-(3-methyl-3H-imidazol-1-ium)-but-1-yl]-3H-imidazolium-di(toluylsulfate) (Formula 3) (MITS) showed specific destruction of Gram-positive cell walls in a concentration-dependent manner. It was found that at a concentration of 247.5 mM neither Gram-negative nor Gram-positive cell walls were destroyed. However, an increase of this concentration by about 50% or more results in the destruction of Gram-positive cell walls. Thus, the present invention provides a lysis solution for Gram-positive bacteria comprising a measured amount of MITS (Formula 3) in the presence of the bacteria, the concentration of MITS (Formula 3) being equal to or higher than 375 mM and up to about 1.7 M.

The ionic liquids capable of destroying a bacterial cell wall comprise amphiphilic ionic compounds. These substances also disrupt biomembranes as well as complexes of biomolecules. Thus, once the cell walls are destroyed, the inner compartments of the cells are lysed by the ionic liquids in the compositions of the present invention.

In EP 1 983 051 it was shown that in the presence of an ionic liquid comprising a 1-butyl-3-methyl-imidazolium cation nucleic acids could be adsorbed to the silica surface of a solid phase. A similar effect was shown for a number of other ionic liquids.

With substantial technical advantage this property can be used for a coupled lysis and extraction step, as described in the Examples 5, 6, and 7. Thus, three different properties of the ionic liquids in the compositions of the invention can be used in one workflow: Firstly the ionic liquids aide in lysing the sample material, either alone or in combination with, e.g., mechanical treatment. Secondly, the ionic liquids act similarly as detergents in that cellular components are solubilized in the lysate. Thirdly, ionic liquids are capable of promoting adsorption of nucleic acids to a silica surface of a solid phase, thereby efficiently facilitating extraction of the nucleic acids. This combination of advantageous features allows the design of efficient sample preparation workflows. Remarkably, in workflows of the state of the art combinations of a chaotropic agent and a detergent can be substituted by a single, more versatile compound, an ionic liquid such as BMIM-SCN (Formula 1).

With the method of nucleic acid purification according to the invention one can process a large number of different biological samples. A preferred sample may contain a plurality of organic and inorganic compounds which are desired to be separated from the nucleic acid. Particularly, the sample can contain leucocytes, and other immunologically active cells, chemical compounds with a low and/or a high molecular weight such as haptens, antigens, antibodies and nucleic acids. The sample can be whole blood, blood serum, blood plasma, cerebral fluid, sputum, stool, biopsy specimens, bone marrow, oral rinses, tissues, urine or mixtures thereof. The present method according to the invention also encompasses biological samples such as a fluid from the human or animal body; preferably the biological sample is blood, blood plasma, blood serum or urine. The blood plasma is preferably EDTA, heparin or citrate blood plasma. Preferably, the biological sample comprises bacterial cells, fungal cells, or mixtures thereof. A preferred fungal cell is a yeast cell.

In yet more detail, the present invention encompasses the following items:

1. A composition comprising an aqueous liquid phase, bacterial cells, and an ionic compound dissolved in the liquid phase at a concentration of about 560 mM or higher, characterized in that the ionic compound is selected from the group consisting of 1-butyl-3-methyl-imidazolium-thiocyanate, 1-butyl-3-methyl-imidazolium-2(2-methoxyethoxy)ethylsulfate, 1-methyl-1-[4-(3-methyl-3H-imidazol-1-ium)-but-1-yl]-3H-imidazolium-di(toluylsulfate), and 1-butyl-3-methyl-imidazolium-octylsulfate.
2. The composition according to item 1, characterized in that the concentration of the ionic compound dissolved in the liquid phase is between about 560 mM and about 2.3 M.
3. The composition according to any of the items 1 and 2, characterized in that the bacterial cells are selected from the group consisting of Gram-positive bacteria and Gram-negative bacteria.
4. A composition comprising an aqueous liquid phase, Gram-negative bacterial cells, and an ionic compound dissolved in the liquid phase at a concentration of about 370 mM or higher, characterized in that the ionic compound is 1-butyl-3-methyl-imidazolium-octylsulfate.
5. The composition according to item 1, characterized in that the concentration of the ionic compound dissolved in the liquid phase is between about 370 mM and about 2.3 M.
6. A composition comprising an aqueous liquid phase, Gram-negative bacterial cells, and an ionic compound dissolved in the liquid phase at a concentration of about 560 mM, characterized in that the ionic compound is 1-butyl-3-methyl-imidazolium-thiocyanate (BMIM-SCN).
7. A composition comprising an aqueous liquid phase, Gram-negative bacterial cells, and an ionic compound dissolved in the liquid phase at a concentration of between about 560 mM and about 2.3 M, characterized in that the ionic compound is selected from the group consisting of 1-butyl-3-methyl-imidazolium-thiocyanate, 1-butyl-3-methyl-imidazolium-2(2-methoxyethoxy)ethylsulfate, and 1-butyl-3-methyl-imidazolium-octylsulfate.
8. The composition according to item 7, characterized in that the concentration of the ionic compound dissolved in the liquid phase is between about 560 mM and about 1.7 M.
9. A composition comprising an aqueous liquid phase, Gram-positive bacterial cells, and an ionic compound dissolved in the liquid phase at a concentration of about 560 mM, characterized in that the ionic compound is 1-methyl-1-[4-(3-methyl-3H-imidazol-1-ium)-but-1-yl]-3H-imidazolium-di(toluylsulfate).
10. A composition comprising an aqueous liquid phase, Gram-positive bacterial cells, and an ionic compound dissolved in the liquid phase at a concentration of about 560 mM or higher, characterized in that the ionic compound is selected from the group consisting of 1-butyl-3-methyl-imidazolium-2(2-methoxyethoxy)ethylsulfate, 1-methyl-1-[4-(3-methyl-3H-imidazol-1-ium)-but-1-yl]-3H-imidazolium-di(toluylsulfate), and 1-butyl-3-methyl-imidazolium-octylsulfate.
11. A composition comprising an aqueous liquid phase, Gram-positive bacterial cells, and an ionic compound dissolved in the liquid phase at a concentration of about 2.3 M or higher, characterized in that the ionic compound is 1-butyl-3-methyl-imidazolium-thiocyanate.
12. A composition according to any of the items 1 to 11, characterized in that the pH of the composition is acidic.
13. The composition according to item 12, characterized in that the acidic pH is between about pH 4 and about pH 6.5.
14. The composition according to item 13, characterized in that the pH is pH 6.
15. A composition according to any of the items 1 to 14, further comprising a buffer salt capable of buffering at an acidic pH.
16. A composition according to any of the items 1 to 15, further comprising a solid phase with a silica surface.
17. The composition according to item 16, characterized in that the solid phase comprises magnetically attractable particles.
18. The composition according to any of the items 16 and 17, characterized in that the ionic compound is 1-butyl-3-methyl-imidazolium-thiocyanate.
19. The composition according to item 18, characterized in that the concentration of the ionic compound in the aqueous liquid phase is about 1.5 M or higher.
20. A composition comprising an aqueous liquid phase, a cell homogenate, and an ionic compound dissolved in the liquid phase at a concentration of about 1.5 M or higher, characterized in that the ionic compound is 1-butyl-3-methyl-imidazolium-thiocyanate.
21. The composition according to item 20, characterized in that the pH of the composition is acidic.
22. A composition according to item 21, further comprising a buffer salt capable of buffering at an acidic pH.
23. A composition according to any of the items 20 to 22, further comprising a solid phase with a silica surface.
24. The composition according to item 23, characterized in that the solid phase comprises magnetically attractable particles.
25. The composition according to any of the items 20 to 25, characterized in that the cell is a bacterial cell or a fungal cell, even more preferred a yeast cell.
26. Use of a composition according to any of the items 1 to 3 for disintegrating, making porous, dissolving, degrading or denaturing the cell wall of a bacterial cell.
27. Use of a composition according to any of the items 4 to 8 for disintegrating, making porous, dissolving, degrading or denaturing the cell wall of a Gram-negative bacterial cell.
28. Use of a composition according to any of the items 9 to 11 for disintegrating, making porous, dissolving, degrading or denaturing the cell wall of a Gram-positive bacterial cell.
29, Use of a composition according to any of the items 1 to 3 and further comprising a solid phase with a silica surface for lysing a bacterial cell and purifying a nucleic acid therefrom.

30. Use of a composition according to item 20 and further comprising a solid phase with a silica surface for lysing a cell homogenate and purifying a nucleic acid therefrom.

31. A method of producing a lysate of a bacterial cell, the method comprising (a) contacting the bacterial cell with, a composition comprising an aqueous liquid phase and an ionic compound dissolved in the liquid phase at a concentration of about 560 mM or higher, whereby the ionic compound is selected from the group consisting of 1-butyl-3-methyl-imidazolium-thiocyanate, 1-butyl-3-methyl-imidazolium-2(2-methoxyethoxy)ethylsulfate, 1-methyl-1-[4-(3-methyl-3H-imidazol-1-ium)-but-1-yl]-3H-imidazolium-di(toluylsulfate), and 1-butyl-3-methyl-imidazolium-octylsulfate, and (b) incubating the bacterial cell with the liquid phase, thereby producing a lysate of the bacterial cell.

32. A method of producing a lysate of a Gram-negative bacterial cell, the method comprising (a) contacting the bacterial cell with a composition comprising an aqueous liquid phase and an ionic compound dissolved in the liquid phase at a concentration of about 370 mM or higher, whereby the ionic compound is 1-butyl-3-methyl-imidazolium-octylsulfate, and (b) incubating the bacterial cell with the liquid phase, thereby producing a lysate of the Gram-negative bacterial cell.

33. A method of producing a lysate of a Gram-negative bacterial cell, the method comprising (a) contacting the bacterial cell with a composition comprising an aqueous liquid phase and an ionic compound dissolved in the liquid phase at a concentration of about 560 mM, whereby the ionic compound is 1-butyl-3-methyl-imidazolium-thiocyanate (BMIM-SCN), and (b) incubating the bacterial cell with the liquid phase, thereby producing a lysate of the Gram-negative bacterial cell.

34. A method of producing a lysate of a Gram-negative bacterial cell, the method comprising (a) contacting the bacterial cell with a composition comprising an aqueous liquid phase and an ionic compound dissolved in the liquid phase at a concentration of between about 560 mM and about 2.3 M, whereby the ionic compound is selected from the group consisting of 1-butyl-3-methyl-imidazolium-thiocyanate, 1-butyl-3-methyl-imidazolium-2(2-methoxyethoxy)ethylsulfate, and 1-butyl-3-methyl-imidazolium-octylsulfate, and (b) incubating the bacterial cell with the liquid phase, thereby producing a lysate of the Gram-negative bacterial cell.

35. A method of producing a lysate of a Gram-positive bacterial cell, the method comprising (a) contacting the bacterial cell with a composition comprising an aqueous liquid phase and an ionic compound dissolved in the liquid phase at a concentration of about 560 mM, whereby the ionic compound is 1-methyl-1-[4-(3-methyl-3H-imidazol-1-ium)-but-1-yl]-3H-imidazolium-di(toluylsulfate), and (b) incubating the bacterial cell with the liquid phase, thereby producing a lysate of the Gram-positive bacterial cell.

36. A method of producing a lysate of a Gram-positive bacterial cell, the method comprising (a) contacting the bacterial cell with a composition comprising an aqueous liquid phase and an ionic compound dissolved in the liquid phase at a concentration of about 560 mM or higher, whereby the ionic compound is selected from the group consisting of, 1-butyl-3-methyl-imidazolium-2(2-methoxyethoxy)ethylsulfate, 1-methyl-1-[4-(3-methyl-3H-imidazol-1-ium)-but-1-yl]-3H-imidazolium-di(toluylsulfate), and 1-butyl-3-methyl-imidazolium-octylsulfate, and (b) incubating the bacterial cell with the liquid phase, thereby producing a lysate of the Gram-positive bacterial cell.

37. A method of producing a lysate of a Gram-positive bacterial cell, the method comprising (a) contacting the bacterial cell with a composition comprising an aqueous liquid phase and an ionic compound dissolved in the liquid phase at a concentration of about 2.3 M or higher, whereby the ionic compound is 1-butyl-3-methyl-imidazolium-thiocyanate, and (b) incubating the bacterial cell with the liquid phase, thereby producing a lysate of the Gram-positive bacterial cell.

38. A method of purifying a nucleic acid from a cell, comprising the steps of (a) destroying the cell wall of the cell if a cell wall is present; (b) contacting and incubating the cell with an acidic aqueous solution comprising 1-butyl-3-methyl-imidazolium-thiocyanate at a concentration of 1.5 M or higher, thereby forming a lysate; (c) contacting the lysate with a solid phase comprising a silica surface, whereby the nucleic acid is adsorbed to the surface; (d) separating the solid phase from the liquid phase and optionally washing the solid phase, whereby the nucleic acid remains adsorbed thereto; and (e) eluting the nucleic acid from the solid phase, thereby purifying the nucleic acid.

Example 1

Microbial Cells

Microbial strains (A) *Staphylococcus carnosus* BMTU 7329, (B) *Escherichia coli* BMTU 3294, and (C) *Candida famata* BMTU 7408 were each cultured separately in liquid culture using minimal media and standard conditions for growth. Cell suspensions containing between about $10^7$ and about $10^8$ cells/ml were prepared.

Example 2

Viability Assessment of Microbial Cells

In order to assess that the cells and the suspensions were living cells, an aliquot of the *Candida famata* cell suspension was analyzed with the LIVE/DEAD® Yeast Viability Kit (Invitrogen Corporation, catalogue no. L7009), and aliquots of the *Staphylococcus carnosus* and the *Escherichia coli* cell suspensions were analyzed with the LIVE/DEAD® BacLight™ Bacterial Viability Kit (Invitrogen catalogue no. L7012).

The LIVE/DEAD® Yeast Viability Kit supplied by Invitrogen combines a two-color fluorescent probe for yeast viability, FUN® 1 cell stain (Molecular Probes), with a fluorescent fungal surface labeling reagent of a third color, Calcofluor™ White M2R (Molecular Probes). Calcofluor is an ultraviolet-excitable dye that can be used as a marker of fungal cell walls.

According to the manufacturer, the FUN® 1 and FUN® 2 viability stains exploit normal endogenous biochemical processing mechanisms that appear to be conserved among different species of yeast and other fungi. The conversion of FUN® 1 and FUN® 2 cell stains from a diffusely distributed pool of green fluorescent intracellular stain to a compact form consisting of orange-red or yellow-orange fluorescent intravacuolar structures, respectively, requires both plasma membrane integrity and metabolic capability. Only metabolically active cells are marked clearly with fluorescent intravacuolar structures (scored as "alive"), while dead cells exhibit extremely bright, diffuse, green-yellow fluorescence (scored as "dead"). Cells with intact membranes but with little or no metabolic activity have diffuse green cytoplasmic fluorescence and lack fluorescent intravacuolar bodies.

The LIVE/DEAD® BacLight Bacterial Viability Kits supplied by Invitrogen utilize mixtures of the SYTO® 9 green-fluorescent nucleic acid stain (Invitrogen) and the red-fluorescent nucleic acid stain, propidium iodide. These stains differ both in their spectral characteristics and in their ability to penetrate healthy bacterial cells. When used alone, the SYTO® 9 stain generally labels all bacteria in a population—those with intact membranes and those with damaged membranes. In contrast, propidium iodide penetrates only bacteria with damaged membranes, causing a reduction in the SYTO® 9 stain fluorescence when both dyes are present.

According to the manufacturer's manual, with the supplied mixture of the SYTO® 9 and propidium iodide stains, bacteria with intact cell membranes stain fluorescent green, whereas bacteria with damaged membranes stain fluorescent red. The excitation/emission maxima for these dyes are about 480/500 nm for SYTO® 9 stain and 490/635 nm for propidium iodide. The background remains virtually nonfluorescent.

A common criterion for bacterial viability is the ability of a bacterium to reproduce in suitable nutrient medium. Exponentially growing cultures of bacteria typically yield results with the LIVE/DEAD® BacLight bacterial viability assay that correlate well with growth assays in liquid or solid media. Under certain conditions, however, bacteria having compromised membranes may be able to recover and reproduce—such bacteria may be scored as "dead" in this assay. Conversely, some bacteria with intact membranes may be unable to reproduce in nutrient medium, and yet these may be scored as "alive."

LIVE/DEAD® assays were performed according to the manufacturer's instructions, if not indicated otherwise. For fluorescence microscopy a Zeiss Axioplan microscope was used.

Treated and untreated microbial cells were additionally analyzed using light microscopy performed with a Leica Laborlux S microscope.

Example 3

Lysis Reagents

TABLE 1

Compositions of lysis reagents

| designation | composition | |
|---|---|---|
| Control 1 | 0.5M | Guanidine thiocyanate (GuaSCN), |
|  | 37.5 mM | TrisHCl, pH 6 |
| Control 2 | 3M | GuaSCN, |
|  | 37.5 mM | TrisHCl, pH 6 |
| L1.1 | 0.5M | 1-butyl-3-methyl-imidazolium-thiocyanate (BMIM-SCN), |
|  | 9.4 mM | TrisHCl, pH 6 |
| L1.2 | 0.75M | BMIM-SCN, |
|  | 14.1 mM | TrisHCl, pH 6 |
| L1.3 | 3M | BMIM-SCN, |
|  | 56.25 mM | TrisHCl, pH 6 |
| L2.1 | 0.75M | 1-butyl-3-methyl-imidazolium-2(2-methoxyethoxy)-ethylsulfate, |
|  | 50 mM | MES, pH 6 |
| L3.1 | 0.5M | 1-methyl-1-[4-(3-methyl-3H-imidazol-1-ium)-but-1-yl]-3H-imidazolium-di(toluylsulfat (MITS), |
|  | 50 mM | MES, pH 6 |
| L3.2 | 0.75M | MITS, |
|  | 50 mM | MES, pH 6 |
| L4.1 | 0.33M | 1-butyl-3-methyl-imidazolium-octylsulfate |
|  | 50 mM | MES, pH 6 |
| L4.2 | 0.5M-2.25M | 1-butyl-3-methyl-imidazolium-octylsulfate |
|  | 50 mM | MES, pH 6 |
| L5.1 | 0.75M-2.25M | 1H-Imidazolium, 3-(4-hydroxybutyl)-1-methyl-toluylsulfat (MHBMIM) |
|  | 50 mM | MES, pH 6 |
| L6.1 | 0.75M-2.25M | 1-Hexyl-3-methyl-imidazolium-bromide |
|  | 50 mM | MES, pH 6 |
| L7.1 | 0.75M-2.25M | N-butyl-pyridinium-chloride |
|  | 50 mM | MES, pH 6 |
| L8.1 | 0.75M-2.25M | N-Hexyl-pyridinium-chloride |
|  | 50 mM | MES, pH 6 |
| L9.1 | 0.75M-2.25M | 3-Carbamoyl-1-octyl-oxymethyl-pyridinium-chloride |
|  | 50 mM | MES, pH 6 |
| L10.1 | 0.75M-2.25M | 1-methyl-1-butyl-pyrrolidinium-tetrafluorborate |
|  | 50 mM | MES, pH 6 |
| L11.1 | 0.75M-2.25M | 1-methyl-l-octyl-pyrrolidinium-chloride |
|  | 50 mM | MES, pH 6 |

All reagents listed above were prepared in water. Further sets of reagents with the same respective composition were prepared, wherein in each of the reagents the only difference was a pH value selected from pH 5.5, pH 5, pH 4.5, and pH 4.

Example 4

Lysis of Microbial Cells, Microscopic Assessment

An aliquot of 200 μl of a cell suspension of microbial cells according to Example 1 was mixed with an aliquot of 600 μl of each lysis reagent according to Example 3. Each mixture was incubated for 15 min at 56° C.

In addition, incubations were made at room temperature for 30 min. Further experiments were performed whereby at a given temperature the time of the incubation with the respective lysis reagent was varied. The influence of the pH value of the lysis reagents was tested by reducing the pH in steps down to a value of pH 4. Essentially, the results obtained under such altered pH conditions were comparable with the results obtained at pH 6.

Before each lysis experiment viability of the undertreated microbial cells was tested following the procedures described in Example 2. For the lysis experiments, all possible combinations of lysis buffers L1.1 to L11.1 with cell suspensions (A), (B), and (C) were examined. Following the incubation of a cell suspension with the respective lysis reagent a viability assessment of the microbial cells in the incubated mixture was performed as described in Example 2.

An incubated cell suspension with bacteria was scored as a "positive" lysate if in the incubated mixture SYTO® 9 stainable morphological structures corresponding to the respective bacterial cells were not detectable. Otherwise, when SYTO® 9 stainable morphological structures were still present, the incubated cell suspension was scored as "negative". In an analogous way, a cell suspension with yeast cells was scored, however based on Calcofluor™ White M2R staining.

In each experiment a direct comparison was made using the fluorescent label on an untreated but similarly diluted cell suspension as a reference. In order to exclude any influence of a compound in the lysis reagents on fluorescence, any presence or absence of morphological structures corresponding to the respective microbial cells was verified using light microscopy. The results are summarized in Table 2.

TABLE 2

Effectiveness of lysis reagents on microbial cells in suspension

| designation | (A) Gram-positive | (B) Gram-negative | (C) chitin cell wall | Concentration of active compound |
|---|---|---|---|---|
| Control 1 | − | − | − | 0.375M |
| Control 2 | + | + | − | 2.25M |
| L1.1 | − | − | − | 0.375M |
| L1.2 | − | + | − | 0.5625M |
| L1.3 | + | + | − | 2.25M |
| L2.1 | + | + | − | 0.5625M |
| L3.1 | − | − | − | 0.375M |
| L3.2 | + | − | − | 0.5625M |
| L4.1 | − | − | − | 0.2475M |
| L4.2$ | − | + | − | 0.375M to 1.6875M |
| L5.1§ | − | − | − | 0.5625M to 1.6875M |
| L6.1§ | − | − | − | 0.5625M to 1.6875M |
| L7.1§ | − | − | − | 0.5625M to 1.6875M |
| L8.1§ | − | − | − | 0.5625M to 1.6875M |
| L9.1§ | − | − | − | 0.5625M to 1.6875M |
| L10.1§ | − | − | − | 0.5625M to 1.6875M |
| L11.1§ | − | − | − | 0.5625M to 1.6875M |

A negative score is represented by "−", a positive score by "+".
$The scores were unchanged with the ionic liquid in the lysis buffer being in the concentration range of about 0.5M to about 2.25M. in the lysis buffer, corresponding to a final concentration in the range of about 0.375M to about 1.6875M in the mixture of the lysis buffer and the cell suspension.
§The scores were unchanged with the ionic liquid in the lysis buffer being in the concentration range of about 0.75M to about 2.25M, corresponding to a final concentration in the range of about 0.5625M to about 1.6875M in the mixture of the lysis buffer and the cell suspension.

It was found that under the conditions described above none of the tested lysis reagents was effective in disintegrating the cell wall structure of C. famata. Surprisingly, only L1.3 and L2.1 had an effect similar to Control 2 containing a chaotropic agent at an high concentration. More surprising, L1.2 and L4.2 exhibited a specificity for lysing Gram-negative cell walls but not Gram-positive cell walls. Even more surprising and completely unexpected, Gram-positive but not Gram-negative cell walls were lysed by L3.2.

Example 5

Lysis of Bacterial Cells Combined with Nucleic Acid Purification Using Spin Columns Bacterial suspensions (A) and (B) were provided as described in Example 1. An aliquot of 200 μl of each cell suspension was mixed with an aliquot of 600 μl of a lysis buffer Control 2 or L1.3 according to Example 3. The mixtures were incubated for 15 min at 56° C. In separate compartments cell suspensions (A) and (B) were incubated.

Each of the lysates was applied to a spin column. To this end, HIGH PURE™ spin columns of the plasmid isolation kit (Roche Applied Science, Article No. 11754777001; Roche Diagnostics GmbH Mannheim) or spin columns of the NucleoSpin Blood kit obtainable from Macherey & Nagel (Cat. No. 740951.50) were used.

After the incubation step at 56° C., the lysed mixture was loaded on a spin column at room temperature. Each column was attached to a sample tube. By centrifugation on a microcentrifuge (e.g., Eppendorf 5415 C) according to the manual of the respective kit the lysate was passed through the glass filter in the column, whereby nucleic acids adsorbed to the glass fleece in the presence of the ionic liquid. The columns were subsequently washed with a washing buffer according to the instructions by the manufacturer of the respective spin column. The adsorbed nucleic acids were eluted from the spin columns using either water or an elution buffer as specified by the manufacturers. The nucleic acids in the eluate were determined spectrophotometrically at 260 nm.

Example 6

Lysis of Bacterial Cells Combined with Nucleic Acid Purification Using Magnetically Attractable Particles Bacterial suspensions (A) and (B) were provided as described in Example 1. An aliquot of 200 μl of each cell suspension was mixed with an aliquot of 600 μl of a lysis buffer Control 2 or L1.3 according to Example 3. The mixtures were incubated for 15 min at 56° C. In separate compartments cell suspensions (A) and (B) were incubated.

Magnetic particles in suspension were taken from a MagNA Pure compact nucleic acid isolation kit I—large volume (Roche Applied Science, Roche Diagnostics GmbH Mannheim, Article No. 03730972001. However, all purification steps were performed manually using conventional Eppendorf® tubes and a magnetic rack for Eppendorf® tubes for applying a magnetic field. An aliquot of 150 μl of particle suspension was mixed with each lysate and incubated at room temperature for 30 sec.

Subsequently, the particles were immobilized by means of a magnetic field and separated from the liquid phase. The particles were washed once with 500 μl of a first aqueous washing buffer consisting of 5 M Guanidinium HCl, 38% [v/v]ethanol, 20 mM Tris HCl, pH 6.6 and twice with 500 μl of a second aqueous washing buffer consisting of 100 mM NaCl, 50% [v/v]ethanol, 10 mM TrisHCl, pH 7.4. Each wash was performed by removing the magnetic field followed by suspending the particles in the respective wash buffer. In order to remove wash buffer, the particles were immobilized again by means of a magnetic field and separated from the liquid phase.

After the last washing step, adsorbed nucleic acids were eluted from the particles by adding to the particles 500 µl elution buffer (10 mM Tris HCl, pH 8 in water) and agitating the particles in the elution buffer by vortexing vigorously. Subsequently, the particles were sedimented by centrifugation and the supernatant with the nucleic acids in solution was recovered. The nucleic acids in the supernatant were determined spectrophotometrically at 260 nm.

What is claimed is:

1. A composition comprising an aqueous liquid phase, bacterial cells, and an ionic compound dissolved in the liquid phase at a concentration of about 560 mM or higher, wherein the ionic compound is 1-butyl-3-methyl-imidazolium-thiocyanate and, with the proviso that the composition does not include a detergent or chaotropic agent.

2. The composition according to claim 1, further comprising a buffer salt capable of buffering at an acidic pH.

3. The composition according to claim 1, wherein the composition has an acidic pH.

4. The composition according to claim 1, further comprising a solid phase with a silica surface.

5. The composition according to claim 4, wherein the solid phase comprises magnetically attractable particles.

6. A composition comprising an aqueous liquid phase, bacterial cells, and an ionic compound dissolved in the liquid phase at a concentration of at least about 560 mM, wherein the ionic compound is 1-butyl-3-methyl-imidazolium-thiocyanate and the bacterial cells are one of Gram-negative cells, Gram-positive cells, and a mixture thereof, with the proviso that the composition does not include a detergent or chaotropic agent.

7. The composition according to claim 6, further comprising a buffer salt capable of buffering at an acidic pH.

8. The composition according to claim 6, wherein the composition has an acidic pH.

9. The composition according to claim 6, further comprising a solid phase with a silica surface.

10. The composition according to claim 9, wherein the solid phase comprises magnetically attractable particles.

* * * * *